United States Patent [19]

Boltze et al.

[11] Patent Number: 4,477,677

[45] Date of Patent: Oct. 16, 1984

[54] PROCESS FOR THE PREPARATION OF 1-(4-CHLOROBENZOYL)-5-METHOXY-2-METHYL-3-INDOLEACETOXYACETIC ACID

[75] Inventors: Karl-Heinz Boltze, Borod; Hans D. Lehnen, Troisdorf, both of Fed. Rep. of Germany

[73] Assignee: Troponwerke GmbH & Co. KG, Cologne, Fed. Rep. of Germany

[21] Appl. No.: 469,676

[22] Filed: Feb. 25, 1983

[30] Foreign Application Priority Data

Feb. 26, 1982 [DE] Fed. Rep. of Germany ....... 3206886

[51] Int. Cl.$^3$ ........................................... C07D 209/28
[52] U.S. Cl. .................................................. 548/501
[58] Field of Search ......................................... 548/301

[56] References Cited

U.S. PATENT DOCUMENTS 3,910,952 10/1975 Boltze et al. ..................... 548/501
3,966,956 6/1976 Boltze et al. ..................... 548/501

FOREIGN PATENT DOCUMENTS 2234651 7/1972 German Democratic Rep. .

Primary Examiner—Glennon H. Hollrah
Assistant Examiner—David B. Springer
Attorney, Agent, or Firm—Sprung Horn Kramer & Woods

[57] ABSTRACT

The invention relates to a process for preparing 1-(4-chlorobenzoyl)-5-methoxy-2-methyl-3-indoleacetoxyacetic acid which comprises reacting an indolecarboxylic acid or its derivatives with a compound of the formula HO—CH$_2$—CO—O—R$^2$ in the presence of an inert organic solvent in a temperature range from −10° C. to 80° C., so that the resulting product is essentially free from the dechlorinated bi-product. The product of the process of the invention is a known anti inflammatory agent.

5 Claims, No Drawings

PROCESS FOR THE PREPARATION OF 1-(4-CHLOROBENZOYL)-5-METHOXY-2-METHYL-3-INDOLEACETOXYACETIC ACID

The present invention relates to a new process, which is chemically original and advantageous, for the preparation of the known 1-(4-chlorobenzoyl)-5-methoxy-2-methyl-3-indoleacetoxyacetic acid (designated I in the following text).

A number of processes have already been disclosed for the preparation of this known compound, compare, for example, DE-OS (German published specification) No. 2,234,651, DE-OS (German published specification) No. 2,257,867 and DE-OS (German published specification) No. 2,943,125. In the known processes, the carboxyl group is initially protected by a benzyl radical, so that catalytic hydrogenation of the benzyl ester in accordance with the reaction scheme below must be carried out in a final reaction step. Reaction scheme

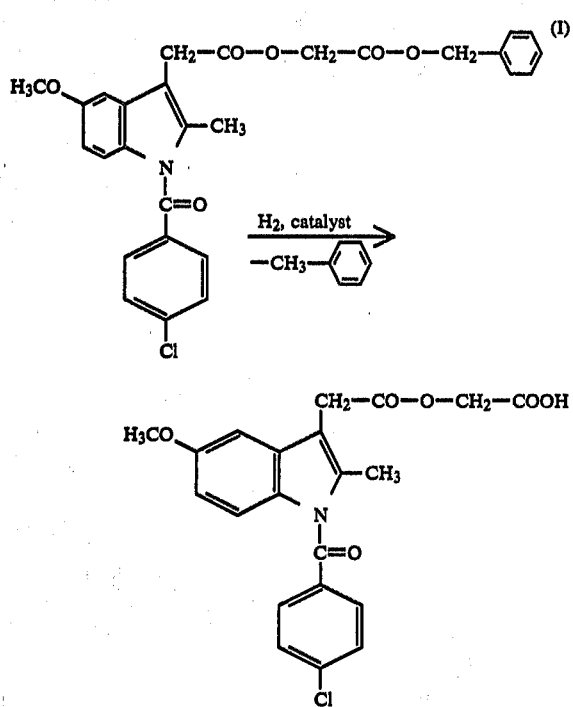

During this removal of the benzyl radical, 1-benzoyl-5-methoxy-2-methyl-3-indoleacetoxyacetic acid, called the dechlorinated compound in the following text, is always produced as a by-product. This undesired impurity, which arises in an amount up to 0.5% by removal of the chlorine from the benzene ring of the 4-chlorobenzoyl radical, must subsequently be removed in elaborate purification steps, and this is associated with losses in yield.

The object of the present invention is to provide an alternative preparation process in which the undesired dechlorinated compound is not produced.

It has been found, surprisingly, that 1-(4-chlorobenzoyl)-5-methoxy-2-methyl-3-indoleacetoxyacetic acid I is obtained in a simple manner and in high purity when indolecarboxylic acid or its derivatives of the general formula II

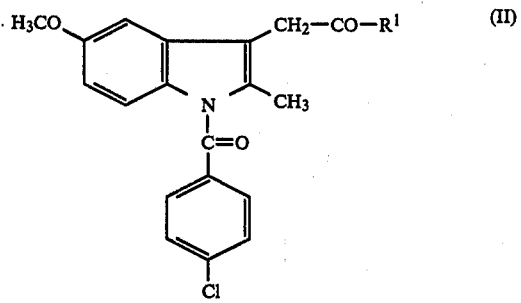

in which $R^1$ represents the radicals

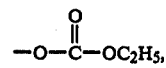

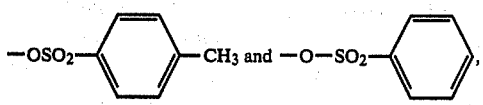

preferably

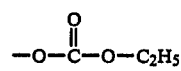

is reacted with compounds of the general formula III

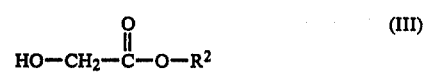

in which $R^2$ represents hydrogen or ammonium, in the presence of inert organic solvents, such as, for example, ethers, diethyl ether, diisopropyl ether, dioxane, tetrahydrofuran, 1,2-dimethoxyethane, chlorinated hydrocarbons, methylene chloride, chloroform, dichloroethane, substituted amides, dimethylformamide, N-methylpyrrolidone, aromatics, toluene, xylene, ketones, acetone, methyl ethyl ketone (2-butanone) in a temperature range from $-10°$ C. to $80°$ C., preferably at $-10°$ to $50°$ C., particularly preferably at $-5°$ C. to $20°$ C.

If, as a representative of the general formula II, the indolecarboxylic acid derivatives, in which $R^1$ denotes the abovementioned substituents, and compounds of the general formula III are used as starting materials, the course of the reaction can be represented by the following reaction scheme:

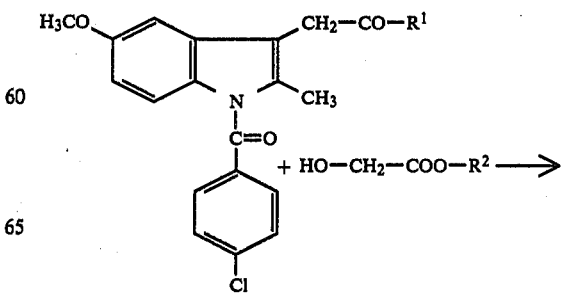

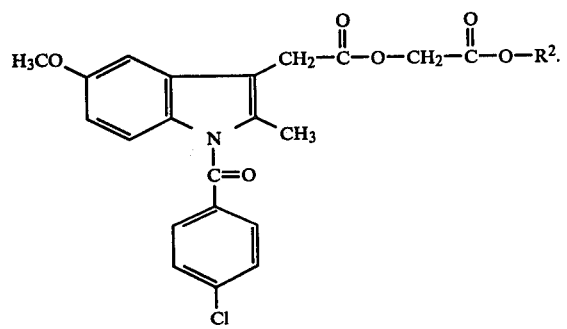

R[1] has the abovementioned meaning, preferably

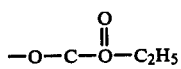

and R[2] has the abovementioned meaning, preferably the ammonium cation. The ammonium compounds produced are subsequently converted into the final product I in a simple manner by treatment with acids.

It was surprising that 1-(4-chlorobenzoyl)-5-methoxy-2-methyl-3-indoleacetoxyacetic acid is produced by this process in such a pure form, that is to say free of the interfering dechlorinated compound, and in yields of 60–70% of theory.

The compounds of the formula II and III used as starting materials are known or are prepared by known processes.

The final compound I prepared by the process according to the invention is a valuable pharmaceutical active substance having an antiinflammatory effect, compare, for example, German patent specification No. 2,234,651.

In the present process, the indolecarboxylic acid II (R[1]=OH) is functionalised by forming the anhydride with, preferably, ethyl carbonate. For this purpose, an ammonium salt of II, preferably the N-methylmorpholinium salt, is reacted with ethyl chloroformate (compare the reaction scheme: synthesis of I). The highly active mixed anhydride, which has not hitherto been disclosed, is isolated and purified.

Its reaction with glycolic acid III (R[2]=H) does not lead to the desired reaction product I. Only when it is in the glycolate form with amines, preferably with diisopropylamine, does reaction of the OH group in the ⊖-position of the glycolic acid occur in the sense of splitting the mixed anhydride with formation of diisopropylammonium 1-(4-chlorobenzoyl)-5-methoxy-2-methyl-3-indoleacetoxyacetate, from which the final compound I is liberated by treatment with acids. Reaction scheme: Synthesis of I (mixed anhydride process) (steps a–d)

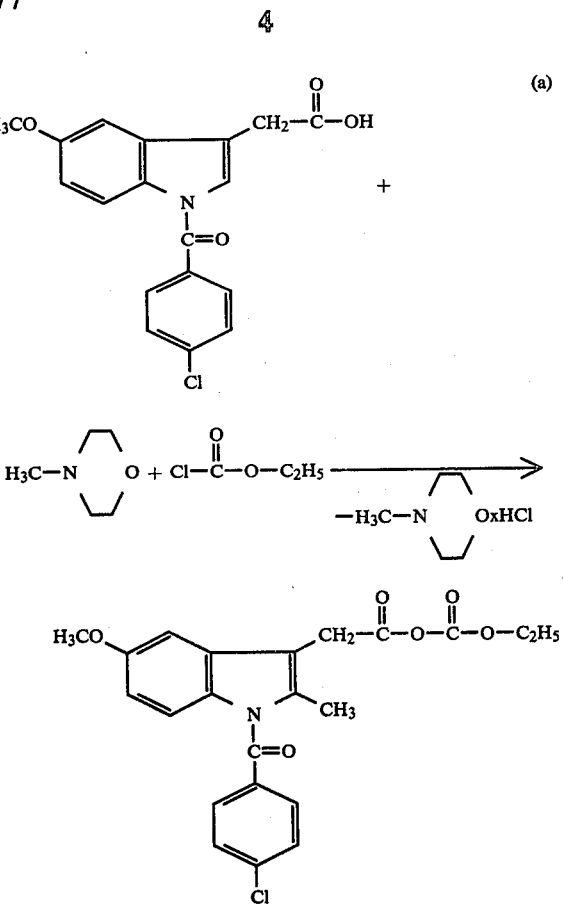

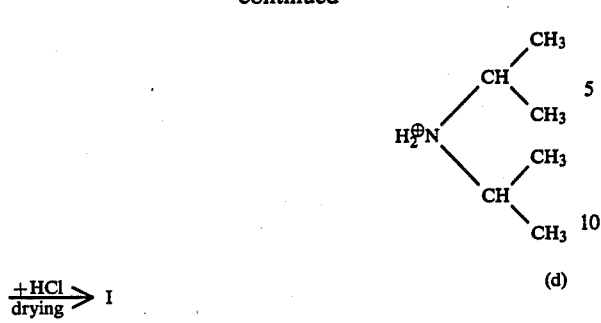

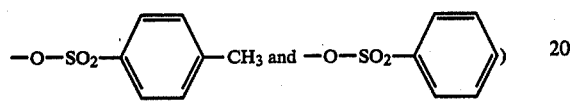

In a further improvement of the process, mixed anhydrides with sulfonic acid esters (II $R^1$-O-$SO_2CH_3$,

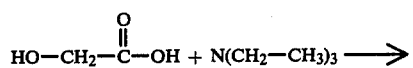

were employed, by using methanesulfonyl chloride, p-toluenesulfonyl chloride and benzenesulfonyl chloride, instead of ethyl chloroformate, for the preparation of the mixed anhydrides.

As an example of these variants, the preparation of I via 1-(4-chlorobenzoyl)-5-methoxy-2-methylindole-3-acetic anhydride with benzenesulfonate (compare reaction scheme) is described. 1. Reaction scheme: Synthesis of I (mixed anhydride process (continuation) (steps a–d)

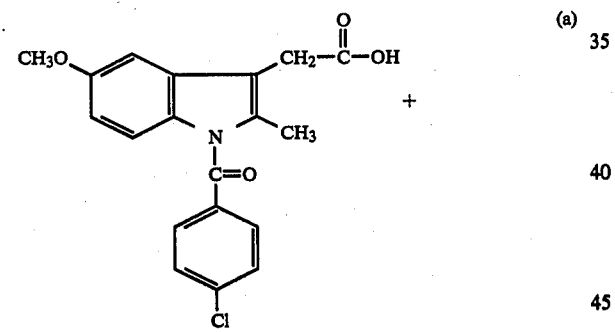

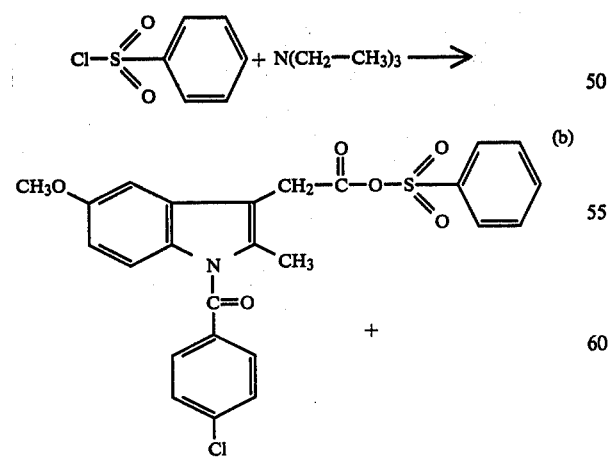

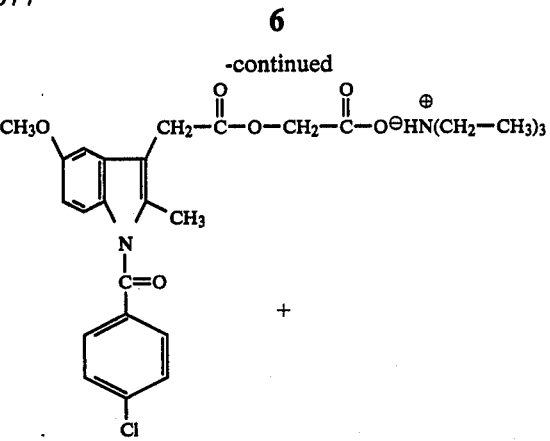

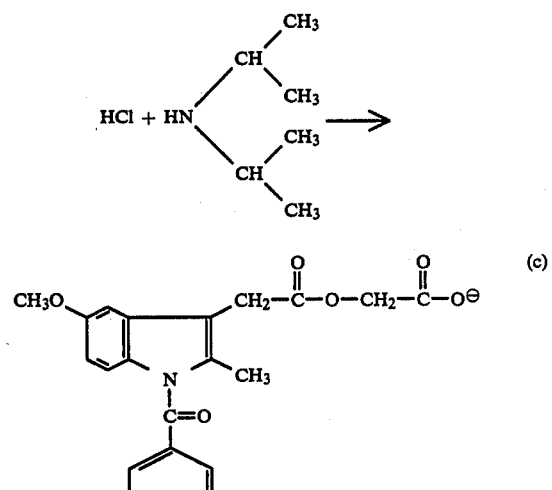

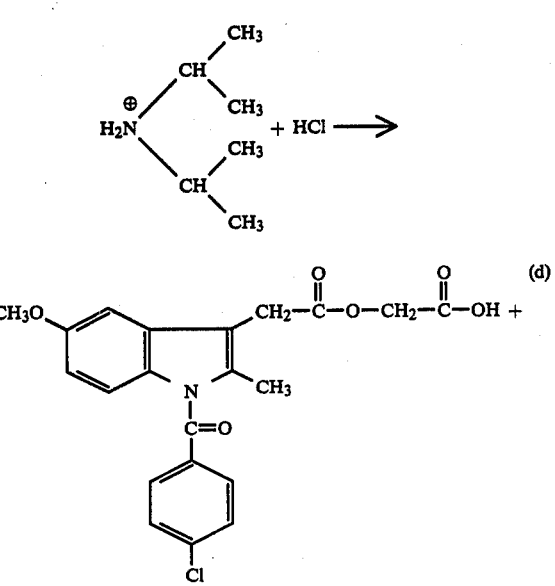

EXAMPLE 1

(a) mixed anhydride II,

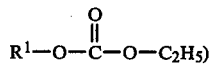

10.8 g of II (R¹OH) (0.03 mol) and 3.3 ml of N-methylmorpholine (0.03 mol) are dissolved in 70 ml of absolute tetrahydrofuran (THF). To this solution, the solution of 3.0 ml of ethyl chloroformate (0.03 mol) in 5 ml of THF is added dropwise, with stirring and exclusion of moisture at about $-10°$ C., and reaction is allowed to continue at $-8°$ C. for 15 minutes.

The precipitated N-methylmorpholinium hydrochloride is removed by filtration and the filtrate is evaporated in a rotary evaporator under water pump vacuum at 20° C. The syrupy residue is taken up with 50 ml of absolute acetone and cooled down to $-15°$ C. with stirring. This produces crystals which are dried over $P_2O_5$.

Yield: 1.7 g of II anhydride (II-O-II) (Symmetrical).

The filtrate is again evaporated at 20° C. in vacuo and the residue is dissolved in 50 ml of absolute ether. After standing at $-15°$ C., crystals form and are dried over $P_2O_5$.

Yield: 9 g of II,

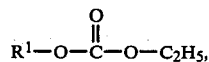

69.7% of theory.

Micro melting point: 74°–75° C. (decomposition).

(b) Diisopropylammonium glycolate 650 ml (4,532 mol) of diisopropylamine are added dropwise at a temperature of about 60° C. to 392 ml (4.0 mol) of glycolic acid III (R²H), with stirring, exclusion of $CO_2$ and cooling. The mixture is heated under reflux for 3 hours (bath temperature 120° C.). The reaction mixture is cooled down to room temperature and 1 l of acetone is added with stirring and the mixture is cooled down to $+5°$ C. After seeding, crystallisation occurs, which is completed with stirring (1 hour). The substance is filtered off and washed twice with 500 ml of acetone each time and dried in a desiccator over $P_2O_5$ at 40° C.

Yield: 625 g of diisopropylammonium glycolate, 88.15% of theory, Mettler FP 61: 79.9° C., colourless crystalline odourless substance.

(c) Diisopropylammonium 1-(4-chlorobenzoyl)-5-methoxy-2-methyl-3-indoleacetoxy acetate 140 ml of ethyl chloroformate (1.4 mol) are dissolved in 1 l of acetone with stirring, and a solution of 504 g of II (R¹OH) (1.408 mol) and 154 ml N-methylmorpholine in 1l of acetone is added at a temperature of 15°–18° C. within 30 minutes. Reaction is allowed to continue at a temperature of $+15°$ C. for 3 minutes and the precipitate formed is filtered off. The residue on the filter is washed twice with 125 ml of acetone each time.

The combined yellow filtrates are then added dropwise, with stirring, at $+25°–27°$ C. within 2.5 hours, to a solution of 413 g of diisopropylammonium glycolate (2.33 mol) in 1 l of $CH_2Cl_2$ and reaction is allowed to take place for 1 hour.

The reaction solution is freed of solvent in a rotary evaporator under water pump vacuum at 30°–40° C. and 3 l of ether are added to the syrupy residue with stirring. Crystallisation occurs after a short time. The colourless crystalline substance is filtered off and washed twice with 1.5 l of ether each time. For purification the substance is dissolved, with stirring under reflux, in 1.5 l of 2-butanone, the solution is left to cool down to room temperature and crystallisation is started by seeding, and is completed by the addition of 3 l of diisopropyl ether.

(d) Conversion into 1-(4-chlorobenzoyl)-5-methoxy-2-methyl-3-indoleacetoxyacetic acid (I)

The ammonium salt (608 g) thus obtained is dissolved, with stirring, in a mixture of 2.42 l of acetone and 0.769 l of $H_2O$.

Then 400 ml NHCl is added to this solution and seeding crystals are added. 1 l NHCl is added dropwise within 1 hour, still at 20° C., (pH: 3) and stirring is continued for 1 hour until crystallisation is complete. The colourless crystalline substance is filtered off with suction, washed with $H_2O$ and dried at 40° C. in water pump vacuum.

Yield: 410 g of I monohydrate=67.1% of theory.

In a drying process at 40° C. (1hour), complete dehydration occurs with the formation of I: yellowish crystals which melted at 151°–152° C.

EXAMPLE 2

(a) Mixed anhydride (II,

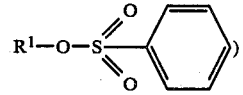

(b) Reaction with triethylammonium glycolate (c) Conversion into the diisopropylammonium salt of I (reaction sequence a–c without isolation of the intermediate products)

A solution of 5.4 g of II (R¹OH)(0.015 mol) and 2.07 ml of triethylamine (0.015 mol) in 20 ml of $CH_2Cl_2$ is added dropwise, with stirring and exclusion of moisture at 0° C., to a solution of 2.9 g of benzenesulphonyl chloride (0.015 mol) in 40 ml of absolute methylene chloride ($CH_2Cl_2$). The reaction is complete in 1½ hours at room temperature. Then a solution of 2.3 g of glycolic acid (0.03 mol) and 4.14 ml of triethylamine (0.03 mol) in 15 ml of $CH_2Cl_2$ is added dropwise within 15 minutes, with stirring, and then stirring is continued a further 19 hours at 28° C. For working up, the reaction solution is acidified with 35 ml of 1 N HCl and then washed twice with 50 ml of $H_2O$ each time. After drying the methylene chloride phase with $Na_2SO_4$, 2.1 ml of diisopropylamine (0.015) are added to the solution and $CH_2Cl_2$ is distilled off in a rotary evaporator. The residue is dissolved in 30 ml of acetone and, after seeding and stirring (1 hour at room temperature), the colourless crystalline substance is filtered off with suction and dried in a desiccator at 40° C.

Yield: 3.6 g of diisopropylammonium 1-(4-chlorobenzoyl-5-methoxy-2-methyl-3-indoleacetoxyacetate.

(d) Conversion into I monohydrate and removal of the water of hydration 3.6 g of the ammonium salt are dissolved in 14 ml of acetone and 4.6 ml of $H_2O$ with stirring. Then 2.6 ml of 1 N HCl are added to this solution and it is seeded. 4.4 ml of 1 N HCl are added dropwise within 1 hour and the mixture is stirred a further 1 hour until crystallisation is complete. The colourless crystalline substance is filtered off with suction, thoroughly washed with $H_2O$ and dried in a desiccator at 40° C. under water pump vacuum.

Yield: 2.3 g of I monohydrate=35.6% of theory.

After drying at 90° under water pump vacuum (1 hour), yellowish crystals are obtained, which melt at 151°-152° C.

In an analogous procedure, the mixed anhydrides

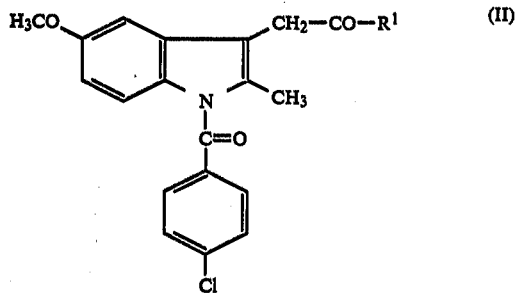

are employed and the final compound I is obtained in 20-53% yield.

We claim:

1. Process for the preparation of 1-(4-chlorobenzoyl)-5-methoxy-2-methyl-3-indoleacetoxyacetic acid (I), characterised in that indolecarboxylic acid or its derivatives of the general formula II

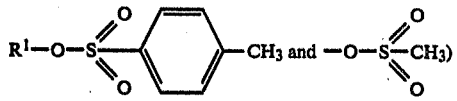 (II)

in which $R^1$ represents the radical

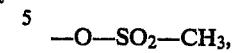

$-O-SO_2-CH_3$,

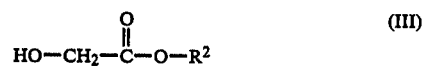

is reacted with compounds of the general formula III $$HO-CH_2-\overset{O}{\underset{\|}{C}}-O-R^2 \qquad (III)$$

in which $R^2$ represents hydrogen or ammonium, in the presence of inert organic solvents in a temperature range from $-10°$ C. to $80°$ C.

2. Process according to claim 1, characterised in that the reaction is undertaken in a temperature range from $-5°$ C. to $20°$ C.

3. Process according to claim 1, characterised in that diethyl ether, diisopropyl ether, dioxane, tetrahydrofuran, 1,2-dimethoxyethane, methylene chloride, chloroform, dichloroethane, dimethylformamide, N-methylpyrrolidone, toluene, xylene, acetone or methyl ethyl ketone are employed as the inert organic solvents.

4. Process according to claim 1 characterised in that $R_1$ denotes

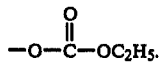

5. Process according to claim 1, characterised in that $R_2$ denotes ammonium.

* * * * *